United States Patent

Sederholm et al.

[11] Patent Number: 5,876,456
[45] Date of Patent: Mar. 2, 1999

[54] IMPLANTABLE PROSTHESIS HAVING INTERFERENCE-LOCKED HOLE PLUGS

[75] Inventors: Gary W. Sederholm, Austin; Eric N. Bachmayer, Marble Falls; Mack D. Morgan, Taylor; Robin L. Ritter, Cedar Park, all of Tex.

[73] Assignee: Sulzer Orthopedics Inc., Austin, Tex.

[21] Appl. No.: 970,226

[22] Filed: Nov. 14, 1997

[51] Int. Cl.⁶ ........................................................ A61F 2/32
[52] U.S. Cl. ................................. 623/16; 623/20; 623/22
[58] Field of Search ................................... 623/16, 18, 19, 623/20, 22, 23

[56] References Cited

U.S. PATENT DOCUMENTS

| | | | |
|---|---|---|---|
| 4,955,325 | 9/1990 | Zarnowski et al. | 623/22 |
| 5,314,487 | 5/1994 | Schryver et al. | 623/22 |
| 5,549,691 | 8/1996 | Harwin | 623/22 |
| 5,571,198 | 11/1996 | Drucker et al. | 623/22 |
| 5,782,929 | 7/1998 | Sederholm | 623/22 |

*Primary Examiner*—David J. Isabella
*Attorney, Agent, or Firm*—Kenneth S. Barrow

[57] ABSTRACT

An implantable orthopedic prosthesis includes a prosthetic component, such as an acetabular shell or tibial baseplate, having a wall. The wall has a first surface for engaging bone and a second surface. The wall defines a hole therethrough extending from the second surface to the first surface. A portion of the hole is oval cylindrical. A plug is provide having a portion that is also oval cylindrical. Each of the oval portions of the hole and plug have respective major and minor transverse axes. The oval cylindrical portion of the plug is sized to fit without interference within the oval portion of the hole if the respective major and minor axes of plug and hole are substantially aligned. The oval portion of the plug fits in locked interference within the oval portion of the hole if the respective major and minor axes of the plug and hole are substantially misaligned. The plug can be freely inserted into and removed from the hole with the respective major and minor axes of the plug and hole substantially aligned. The plug can be interference-locked in the hole by rotating the plug relative to the hole to render the respective major and minor axes of the plug and hole substantially misaligned.

18 Claims, 4 Drawing Sheets ial bone includes a relatively hard outer layer of cortical bone and a relatively soft inner core of cancellous bone. The reaming process removes primarily cancellous bone, and may remove a small amount of cortical bone, to form a substantially hemispherical concavity in the acetabular bone. Reamers of increasing diameter may be used in succession to obtain a hemispherical concavity of a desired diameter for receipt of the acetabular cup.

IMPLANTABLE PROSTHESIS HAVING INTERFERENCE-LOCKED HOLE PLUGS

BACKGROUND OF THE INVENTION

1. Field of the Invention

The present invention relates generally to implantable prostheses for replacing human skeletal joints, and relates more particularly to a prosthetic component having one or more holes therethrough for receipt of a bone screw or instrument.

2. Background Information

Implantable orthopedic prostheses, in one form, comprise man-made replacements for the ends and articulating surfaces of the bones of the skeleton. Such prostheses are implanted to repair or reconstruct all or part of an articulating skeletal joint that is functioning abnormally due to disease, trauma, or congenital defect. Among the various articulating skeletal joints of the human body that are eligible to be fitted with implantable orthopedic prostheses, the hip joint and the knee joint are most often treated with such prostheses. The hip and knee joints are major weight bearing joints and degenerate more quickly than other joints in the event of abnormality. Also, the hip and knee joints play a critical role in ambulation and quality of life, resulting in great demand for surgical correction of abnormalities.

The human hip joint involves two bones: the femur and the pelvis, each having a smooth articulation surface arranged for articulation against an adjacent articulation surface of the other bone. The femur includes at its proximal extremity a head having a convex, generally spherically contoured articulation surface. The pelvis, in pertinent part, includes an acetabulum having a concave, generally spherically contoured articulation surface. The mutually engaging articulation surfaces of the femur and the pelvis together form, functionally, a ball-and-socket joint.

One or both of the articulation surfaces of the hip joint may fail to perform properly, requiring the defective natural articulation surface to be replaced with a prosthetic articulation surface provided by an implantable prosthesis. To accommodate defects of varying scope, while permitting healthy portions of the hip joint to be conserved, a range of types of orthopedic implants is available. The range extends from total hip prosthesis systems for replacing the articulation surfaces of both the femur and the pelvis, to less comprehensive systems for replacing only the femoral articulation surface. Commonly employed orthopedic hip prostheses include components that fall within one of three principle categories: femoral stems, femoral heads and acetabular cups. A so-called "total" hip prosthesis includes components from each of these categories. The femoral stem replaces the proximal end of the femur and includes a distal stem that is received within the medullary canal at the proximal end of the femur. The femoral head replaces the natural head and articulating surface of the femur. The acetabular cup replaces the natural socket and articulating surface of the acetabulum of the pelvis. In some designs, the stem and head are an integral, unitary component, but more often the stem and head are separate modular components designed to be assembled together to suit the anatomical needs of the patient. A so-called "bipolar" hip prosthesis includes only femoral stem and head components. The femoral part of the hip joint is replaced with a femoral stem supporting an artificial femoral head. The latter includes an inner head, fixed to the femoral stem, that articulates within an outer head. The outer head articulates directly against the natural acetabulum. Similarly, a so-called "unipolar" hip prosthesis also includes only femoral stem and head components. The femoral part of the hip joint is replaced with a femoral stem supporting an artificial femoral head. The femoral head articulates directly against the natural acetabulum while remaining fixed relative to the femoral stem.

The human knee joint involves three bones: the femur, the tibia and the patella, each having smooth articulation surfaces arranged for articulation on an adjacent articulation surface of at least one other bone. The femur includes at its distal extremity an articulation surface having medial and lateral convex condyles separated posteriorly by an intercondylar groove running generally in the anterior-posterior direction, the condyles joining at the distal-anterior face of the femur to form a patellar surface having a shallow vertical groove as an extension of the intercondylar groove. The patella includes on its posterior face an articulation surface having a vertical ridge separating medial and lateral convex facets, which facets articulate against the patellar surface of the femur and against the medial and lateral condyles during flexion of the knee joint, while the vertical ridge rides within the intercondylar groove to prevent lateral displacement of the patella during flexion. The tibia includes at its proximal end an articulation surface having medial and lateral meniscal condyles that articulate against the medial and lateral condyles, respectively, of the femur. The mutually engaging articulation surfaces of the femur and the patella together form, functionally, the patellofemoral joint, and the mutually engaging articulation surfaces of the femur and tibia together form, functionally, the tibiofemoral joint, which two functional joints together form the anatomical knee joint.

All or part of one or more of the articulation surfaces of the knee joint may fail to perform properly, requiring the defective natural articulation surface to be replaced with a prosthetic articulation surface provided by an implantable prosthesis. To accommodate defects of varying scope, while permitting healthy portions of the knee joint to be conserved, a range of types of orthopedic knee implants is available. The range extends from total knee prosthesis systems for replacing the entire articulation surface of each of the femur, tibia and patella, to less comprehensive systems for replacing only the tibiofemoral joint, or only one side (medial or lateral) of the tibiofemoral joint, or only the patellofemoral joint. Commonly employed orthopedic knee prostheses include components that fall within one of three principle categories: femoral components, tibial components, and patellar components. A so-called "total" knee prosthesis includes components from each of these categories. The femoral component replaces the distal end and condylar articulating surfaces of the femur and may include a proximal stem that is received within the medullary canal at the distal end of the femur. The tibial component replaces the proximal end and meniscal articulating surfaces of the tibia and may include a distal stem that is received within the medullary canal at the proximal end of the tibia. The patellar component replaces the posterior side and natural articulating surface of the patella. Sometimes, the patellar component is not used, and the natural articulating surface of the patella is allowed to articulate against the femoral component. A so-called "unicondylar" knee prosthesis replaces only the medial or the lateral femoral condylar articulating surface and the corresponding tibial meniscal articulating surface.

The acetabular cup component of a total hip prosthesis is configured to be received and fixed within the acetabulum of a pelvis. The pelvis is prepared to receive the acetabular cup by reaming a concavity in the acetabular bone. The acetabular cup component typically has an outer surface conforming to the concavity reamed in the acetabular bone of the pelvis, and an inner bearing cavity for receiving the head of the femoral component. The head articulates in the bearing cavity as a ball-and-socket joint to restore motion to a defective hip joint.

One known type of acetabular cup involves an acetabular shell made of a bio-compatible metal such as titanium or a titanium alloy, and a bearing insert made of a bio-compatible polymer such as ultra-high molecular weight polyethylene. The acetabular shell is shaped generally as a hemispherical cup having a dome, or apex, at a proximal end and an annular rim at a distal end. As used herein, the words proximal and distal are terms of reference that indicate a particular portion of a prosthesis component according to the relative disposition of the portion when the component is implanted. "Proximal" indicates that portion of a component nearest the torso, whereas "distal" indicates that portion of the component farthest from the torso. Between the dome and rim, the acetabular shell comprises a shell wall defined by a generally convex proximal surface and a generally concave distal surface spaced from the proximal surface. The concave distal surface defines a shell cavity having an opening at the rim of the cup for receiving the bearing insert. The bearing insert has a generally convex proximal surface configured to be received and fixed within the acetabular shell in generally congruent engagement with the concave distal surface of the shell wall. The bearing insert also has a bearing cavity that opens distally for receiving the head of the femoral component. The bearing cavity is defined by a generally spherical concave bearing surface having a radius similar to that of the femoral head component. The concave bearing surface articulates against the surface of the spherical femoral head component.

Acetabular shells of the type described can be affixed to the acetabular bone by bone screws or bone cement. If bone screws are elected, the screws are driven into the bone through the screw holes before the bearing insert is placed into the shell. The shell also can be affixed by a combination of bone screws and bone cement. The acetabular shell can be provided with more screw holes than typically would be used by the implanting physician. This provides a selection of sites for placement of the bone screws, as may be dictated by the condition of the patient's pelvic bone or by the physician's preference. Some of the provided screw holes may receive a screw while others do not. For reasons explained below, it is desirable to provide means for occluding those screw holes that will not receive a screw.

Commonly, acetabular shells of the type described also include a dome hole at the apex. A typical dome hole is coaxially aligned with the axis of symmetry of the acetabular shell and extends through the shell wall from the concave distal surface to the convex proximal surface of the acetabular shell. Often, the dome hole is internally threaded or otherwise configured for receiving an instrument for holding and positioning the acetabular shell during implantation. Also, many physicians use the dome hole to obtain visual or tactile access to the reamed acetabular bone during implantation of the acetabular shell. Such access allows the physician to confirm that the acetabular shell is fully seated in engagement with the reamed bony surface of the acetabulum. As with the screw holes, for reasons explained below, it is also desirable to provide means for occluding the dome hole.

The bearing insert is usually designed to be received within the acetabular shell and may include locking tabs or other means for fixing the bearing insert into the shell in nonarticulating relative relationship. Nevertheless, a small amount of unintended relative motion is believed to occur between the bearing insert and the acetabular shell in response to the varying load borne by the acetabular cup during use. Such small relative motion, or micro-motion, may result in wear at the interface between the bearing insert and acetabular shell that generates fine polyethylene or metal debris. According to some hypotheses, such debris can migrate out of the acetabular cup and contact bone, possibly resulting in osteolysis, which ultimately can lead to bone resorption and possible loosening of the acetabular prosthesis. One apparent pathway for the migration of debris out of the acetabular shell is through open screw holes. Another apparent pathway is through an open dome hole.

The tibial component of a total knee prosthesis is configured to be received upon and fixed to the proximal end of the tibia. The tibia is prepared to receive the tibial component by resecting a portion of the proximal end of the tibia to leave a substantially horizontal planar bony plateau. Sometimes the exposed medullary canal at the proximal end of the tibia is also reamed to receive a stem portion of the tibial component. The tibial component typically includes a plate portion having an inferior planar surface conforming to the resected bony plateau at the proximal end of the femur. The plate portion may or may not include a stem or keel for receipt withing a prepared tibial medullary canal. Commonly, a meniscal bearing insert is received atop the plate portion of the tibial component to provide an artificial meniscal articulating surface for receiving the condylar surfaces of the femoral component of the total hip prosthesis. The femoral condylar articulating surfaces articulate against the tibial meniscal articulating surface to restore motion to a defective knee joint.

One known type of tibial component involves a tibial plate made of a bio-compatible metal such as titanium or a titanium alloy, and a meniscal bearing insert made of a bio-compatible polymer such as ultra-high molecular weight polyethylene. The tibial plate is shaped generally as a flat plate having a perimeter that generally conforms to the transverse sectional perimeter of the resected proximal tibia. The tibial plate includes a planar distal, or inferior, surface for engaging the resected proximal tibia, and a proximal, or superior, surface for engaging and receiving the meniscal bearing insert. One or more screw holes may extend through the plate portion from the superior to the inferior surface. The bearing insert has an inferior surface that engages the superior surface of the plate portion, and may include locking tabs or other means for fixing the bearing insert to the plate portion against relative movement.

Tibial plates of the type described can be affixed to the resected tibial bone by bone screws or bone cement. If bone screws are elected, the screws are driven into the bone through the screw holes before the bearing insert is placed atop the plate portion. The plate also can be affixed by a combination of bone screws and bone cement. Sometimes the plate can be provided with more screw holes than typically would be used by the implanting physician. This provides a selection of sites for placement of the bone screws, as may be dictated by the condition of the patient's tibial bone or by the physician's preference. Some of the provided screw holes may receive a screw while others do not. For reasons similar to those discussed above with regard to acetabular shells, it is desirable to provide means for occluding those screw holes that will not receive a screw.

The tibial bearing insert usually is designed to be received atop the tibial plate in nonarticulating relative relationship. Nevertheless, a small amount of unintended relative motion is believed to occur between the bearing insert and the tibial plate in response to the varying load borne by the tibial component during use. Such small relative motion, or micromotion, may result in wear at the interface between the bearing insert and acetabular shell that generates fine polyethylene or metal debris, similarly to the hypothesized phenomenon discussed above with regard to acetabular shells. One apparent pathway for the migration of debris from the superior surface of the tibial plate is through open screw holes. In some total knee prostheses, the bearing insert is intended to articulate relative to the tibial plate in sliding or rotating relationship. Such knee prostheses are known as "mobile bearing" knees. The possibility of wear debris being generated in such knee prostheses is apparent.

SUMMARY OF THE INVENTION

According to one aspect of the present invention, an implantable orthopedic prosthesis includes a prosthetic component having a wall. The wall has a first surface for engaging bone and a second surface. The wall defines a hole therethrough extending from said second surface to said first surface. At least a portion of the hole is non-circular in transverse cross-section, having a major axis and a minor axis. A plug is provided, at least of portion of which is non-circular in transverse cross-section, having a major axis and a minor axis. The portion of the plug is sized to fit without interference within the portion of the hole if the respective major and minor axes of the plug and hole are substantially aligned. The portion of the plug is sized to fit in locked interference within the portion of the hole if the respective major and minor axes of the plug and hole are substantially misaligned. The plug can be freely inserted into and removed from the hole with the respective major and minor axes of the plug and hole substantially aligned. The plug can be interference-locked in the hole by rotating the plug relative to the hole to make the respective major and minor axes of the plug and hole substantially misaligned.

It is an object of the present invention to provide an implantable orthopedic prosthesis, for engagement with bone, having one or more holes therethrough, which hole can be selectively occluded with a plug to prevent migration of wear debris therethrough.

Other objects and advantages of the present invention will be apparent from the following descriptions of the preferred embodiment illustrated in the drawings.

DESCRIPTION OF THE PREFERRED EMBODIMENTS

Figure 2:
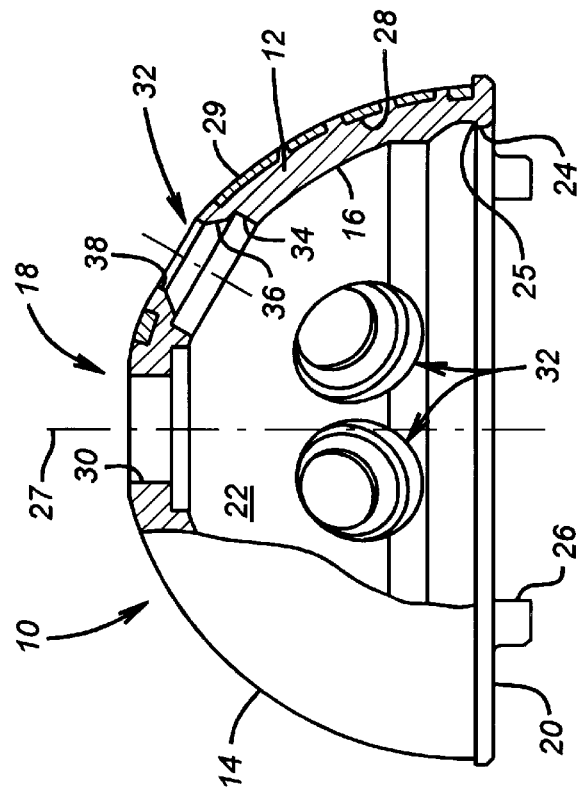
FIG. 2 is a partial sectional view of the acetabular shell of FIG. 1, taken in the plane of the axis of the acetabular shell.

Referring to the drawings, FIGS. 1–8, a preferred embodiment of the present invention is illustrated in the form of an implantable orthopedic prosthesis, particularly an acetabular shell component of a total hip joint prosthesis. The illustrated acetabular shell is useful as one component of that well-known type of total hip joint prosthesis that includes an acetabular shell and an associated bearing liner, and a femoral stem and an associated spherical head. The spherical head, fixed to the femoral stem, articulates in a ball-and-socket arrangement within the bearing liner, with the bearing liner being essentially fixed within the acetabular shell. The femoral stem and acetabular shell are fixed to bone of the proximal femur and pelvic acetabulum, respectively. Only the acetabular shell is described in detail herein, as the various types and configurations of bearing liners and the means for affixing such bearing liners within an acetabular shell are well understood in the art. The illustrated acetabular shell is particularly advantageous for preventing potentially osteolytic polyethylene particles from migrating out of the acetabular shell, when used with a bearing liner made of ultra-high molecular weight polyethylene. The utility of the invention is not limited to the use of any particular bearing liner material, however.

Figure 1:
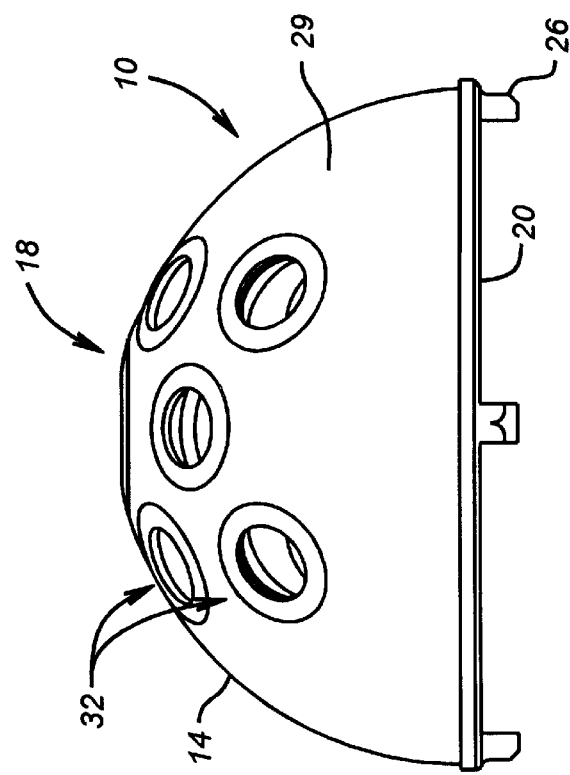
FIG. 1 is an elevation view of an acetabular shell constructed in accordance with the present invention.

Referring to FIGS. 1 and 2, an acetabular shell 10 is shaped generally as a hemispherical cup having a shell wall 12 defined by a convex proximal surface 14 and a concave distal surface 16. Acetabular shell 10 has a proximal dome region 18 at the apex of shell wall 12 and an annular rim 20 at the distal end of shell wall 12. Concave distal surface 16 of shell wall 12 defines a shell cavity 22 having an opening 24 into and through which a bearing insert (not shown) can be received. The preferred bearing insert is made of ultra high molecular weight polyethylene and has a partially spherical bearing cavity that opens distally for receiving a spherical head of a femoral component (not shown) in a ball-and-socket articulating relationship. An annular lip 25 extending radially inwardly from concave distal surface 16, in cooperation with an annular protrusion on the bearing insert, provides a means for affixing the bearing insert against axial displacement within shell cavity 22. Such means also includes an annular flange on the bearing insert having notches for receiving the legs 26 that extend radially from rim 20. The interengagement of the legs 26 and the notches of the bearing insert flange affix the bearing insert against rotation within shell cavity 22. Shell wall 12 is generally symmetrical about an axis 27 that passes through the center of proximal dome region 18 at the apex of shell wall 12. Convex proximal surface 14 is provided with a macro-texture comprising circumferential grooves 28 filled and covered with a porous coating 29 comprised of sintered titanium powder. The porous coating 29 accepts the ingrowth or ongrowth of bone, and enhances adhesion of bone cement. The porous coating 29, while preferred, is not necessary for the understanding or practice of the present invention.

Referring again to FIG. 2, acetabular shell 10 includes a dome hole 30 centered at the apex of dome region 18 in coaxial alignment with axis 27. Dome hole 30 is internally threaded to serve as an engagement interface for an instrument (not shown) for holding and positioning acetabular shell 10. Typically, such an instrument is used by the implanting physician to securely grasp the acetabular shell and place it in the reamed acetabulum. Such an instrument usually includes an elongate handle for controlling anteversion and adduction of the acetabular shell as it is implanted, and for transmitting axial driving forces to the shell.

Still referring to FIG. 2, and also to FIG. 1, acetabular shell 10 is provided with a plurality of screw holes 32 disposed in various locations. The screw holes 32 are provided in superabundance relative to the number of bone screws usually employed to implant the acetabular shell. Hence, the physician is presented with a selection of variously placed screw holes from which to choose. Those screw holes 32 that are not selected by the physician to receive a bone screw will be occluded during the course of the implanting procedure, in accordance with the present invention. Occlusion of unused screw holes 32 is desirable to alleviate the risk of polyethylene debris migrating from shell cavity 22 through open screw holes 32. Such polyethylene debris, according to a prevailing hypothesis, can be generated by frictional wear caused by micro-motion between the acetabular shell and its polyethylene bearing liner. By design, the polyethylene liner is intended to fit congruently against concave distal surface 16, without any articulation relative to the acetabular shell 10. Nevertheless, according to the hypothesis, some relative micro-motion inevitably occurs. The reason for concern over such polyethylene wear debris is that in vitro experiments have shown that fine polyethylene particles are osteolytic.

Each screw hole 32, beginning at concave distal surface 16 and progressing through shell wall 12 to convex proximal surface 14, includes a substantially cylindrical first portion 34, followed by a concave spherical second portion 36, followed finally by another substantially cylindrical third portion 38. As used herein, the term "cylindrical" refers broadly to the geometric surface generated by a line held parallel to an axis while traversing a closed path about the axis, as opposed to the more narrow common usage in which "cylindrical" refers to the special case in which the closed path is a circle. The cylindrical first portion 34 is an oval cylinder, whereas the cylindrical third portion 38 is a circular cylinder, the significance of which will be explained further below.

Figure 3:
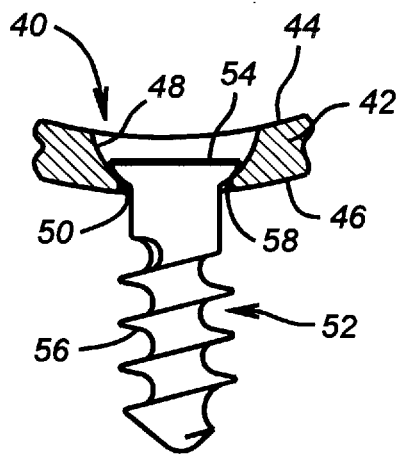
FIG. 3 is a detail sectional view of a prior art screw hole of a typical acetabular shell, and a bone screw received within the screw hole.

Referring to FIG. 3, a prior art screw hole 40 in a typical acetabular shell wall 42 is illustrated. Prior art screw hole 40, beginning at the concave surface 44 of the shell wall 42 and progressing toward the convex surface 46 of the shell wall 42, includes a first concave spherical portion 48 followed by a circular cylindrical portion 50. Prior art bone screw 52 includes a head 54 and a threaded shank 56. The undersurface 58 of head 54 is convexly spherically shaped, with substantially the same radius of curvature as that of spherical portion 48 of screw hole 40. This allows congruent contact to be maintained between the undersurface 58 of bone screw 52 and spherical portion 48 of screw hole 40 despite angular misalignment of the shank 56 relative to the axis of screw hole 40.

Figure 4:
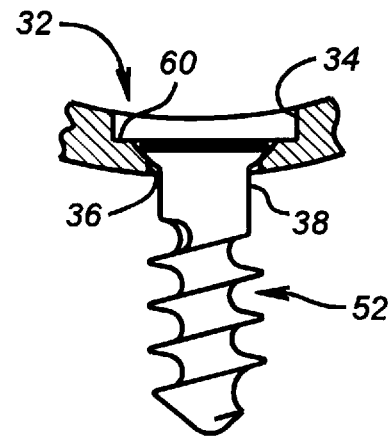
FIG. 4 is a detail sectional view of a screw hole of the acetabular shell of FIG. 1, and a bone screw received within the screw hole.

Referring to FIG. 4, the screw hole 32 of the present invention is illustrated in comparison to the prior art screw hole 40 of FIG. 3, when receiving the same prior art bone screw 52 as illustrated in FIG. 3. The primary difference between the screw hole 32 of the present invention and the prior art screw hole 40 of FIG. 3 is the addition of an oval cylindrical counterbore, previously described as cylindrical first portion 34. Oval cylindrical counterbore 34 terminates at shoulder 60 at a location distal of head 54 of bone screw 52 when bone screw 52 is received in engagement with concave spherical surface 36 of screw hole 32.

Figure 5A:
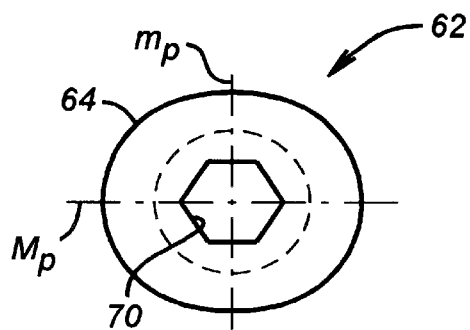
FIG. 5A is a distal end view of a screw hole plug constructed in accordance with the present invention.
Figure 5B:
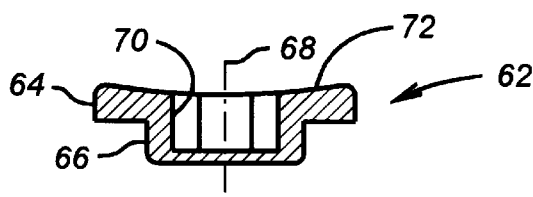
FIG. 5B is a sectional view of the screw hole plug of FIG. 5A taken in the plane 5B—5B of FIG. 5A and viewed in the direction of the arrows.
Figure 5C:
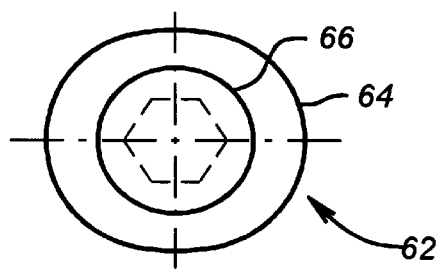
FIG. 5C is a proximal end view of the screw hole plug of FIG. 5A.

Referring to FIGS. 5A, 5B and 5C, a screw hole plug 62 is illustrated that is particularly useful in combination with the screw hole 32 of acetabular shell 10. Screw hole plug 62 includes a first cylindrical portion 64 and a second cylindrical portion 66, both coaxial relative to longitudinal axis 68. First cylindrical portion 64 is an oval cylinder having a major axis $M_p$ and a minor axis $m_p$. In cross-section, first cylindrical portion 64 comprises two arc-sections of common radius, each subtending 180°, connected by short, straight side walls parallel to the major axis $M_p$. Second cylindrical portion 66 is, in cross-section, circular. A blind hole 70, hexagonal in cross-section, extends through oval cylindrical portion 64 and partially through circular cylindrical portion 66. Distal end 72 of screw hole plug 62 is concavely spherical, having a radius of curvature substantially similar to that of concave distal surface 16 of acetabular shell 10.

Figure 6A:
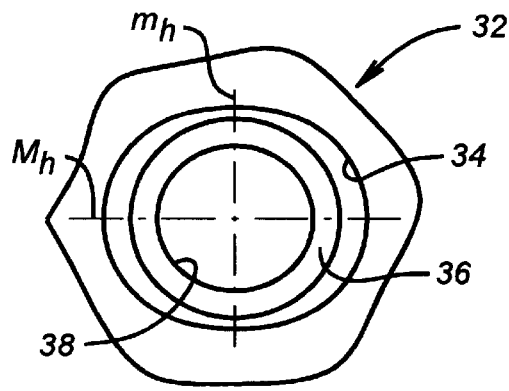
FIG. 6A is an axial view of a screw hole of the acetabular shell of FIG. 1 viewed from the concave distal side of the acetabular shell.
Figure 6B:
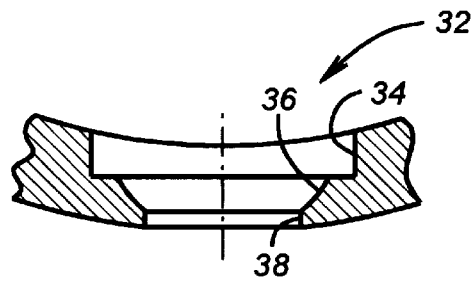
FIG. 6B is a sectional view of the screw hole of FIG. 6A taken in the plane 6B—6B of FIG. 6A and viewed in the direction of the arrows.

Referring to FIGS. 6A and 6B, screw hole 32, as previously described with reference to FIG. 2, is shown in greater detail. Oval cylindrical counterbore 34, also referred to as oval first cylindrical portion 34, has a major axis $M_h$ and a minor axis $m_h$. In cross-section, cylindrical counterbore 34 comprises two arc-sections of common radius, each subtending 180°, connected by short, straight side walls parallel to the major axis $M_p$. Concave spherical portions 36 and cylindrical portion 38 are, in cross section, circular.

Figure 7A:
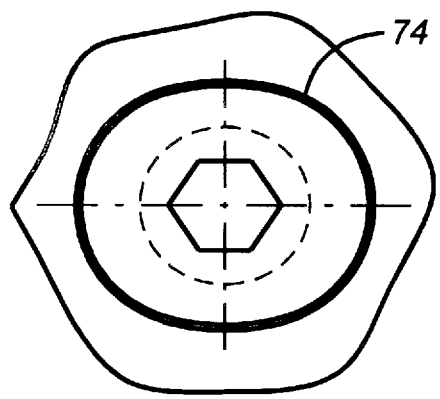
FIG. 7 is an axial view of a screw hole of the acetabular shell of FIG. 1, viewed from the concave distal side of the acetabular shell, in which is received the screw hole plug of FIG. 5A, particularly showing the screw hole plug in a first orientation relative to the screw hole.
Figure 7B:
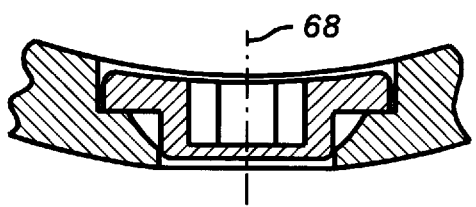

With particular reference to FIGS. 7A and 7B, and 8A and 8B, the interaction of screw hole plug 62 and screw hole 32 is illustrated. In FIGS. 7A and 7B, screw hole plug 62 has been placed within screw hole 32 with the respective major axes Mp and Mh, and minor axes mp and mh, aligned. Oval cylindrical portion 64 of screw hole plug 62 is received within oval cylindrical portion 34 of screw hole 32, and circular cylindrical portion 66 of screw hole plug 62 is received within circular cylindrical portion 38 of screw hole 32. In this first orientation, the dimensions of the oval cylindrical portion 64 of screw hole plug 62 in the directions of its respective major and minor axes are less than the corresponding dimensions of the oval cylindrical portion 34 of screw hole 32 in the directions of its respective major and minor axes. It is preferred that the dimensional differences between the portion 64 and portion 34 be substantially constant to provide an even gap 74 therebetween. Circular cylindrical portion 66 of screw hole plug 62 has a diameter less than the diameter of circular cylindrical portion 38 of screw hole. It is preferred that the diametrical difference between portions 66 and 38 be sufficiently great to permit easy insertion of screw hole plug 62 within screw hole 32, yet sufficiently small to permit portion 66 of screw hole plug 62 to be piloted within portion 38 of screw hole 32 with respect to rotation about axis 68, as described below.

Figure 8A:
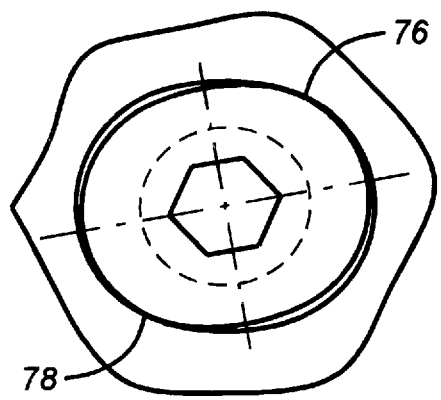
FIG. 8 is an axial view of a screw hole of the acetabular shell of FIG. 1, viewed from the concave distal side of the acetabular shell, in which is received the screw hole plug of FIG. 5A, particularly showing the screw hole plug in a second orientation relative to the screw hole.
Figure 8B:
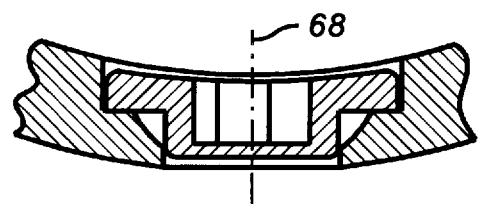

With particular reference to FIGS. 8A and 8B, screw hole plug 62 has been rotated into a second orientation, relative to the first orientation of FIGS. 7A and 7B. In this second orientation, the screw hole plug 62 is disposed relative to the screw hole 32 such that the respective major axes Mp and Mh, and minor axes mp and mh, are not aligned. Screw hole plug 62 has been rotated about axis 68 through an angle of about 10° to about 20°, until portion 64 engages portion 34, at diametrically opposite points 76 and 78, in a wedged, locking interference fit. The perimetrical surfaces of portion 64 and portion 34 converge at a small angle at points 76 and 78, resulting in a circumferentially long area of wedged engagement, which generates a high frictional resistance to the displacement of screw hole plug 62 in either the axial or circumferential directions.

The rotation of screw hole plug 62 from the first orientation of FIGS. 7A and 7B, to the second interference-locked orientation of FIGS. 8A and 8B, is preferably effected by inserting the hexagonal driving end of a hand tool within hexagonal hole 70 and imparting rotary motion to screw hole plug 62 about axis 68 relative to screw hole 32 until a firm interference lock is obtained. If desired, a torque measuring instrument can be employed to monitor the degree of interference to prevent overtightening or undertightening screw hole plug 62. The procedure is reversible, in that an interference-locked screw hole plug 62 can be removed from screw hole 32 by applying the rotary motion in reverse to return the respective major and minor axes of the screw hole plug 62 and screw hole 32 into alignment, whereupon the screw hole plug 62 can be withdrawn from screw hole 32. Preferably, the hexagonal driving end of the hand tool fits with a small amount of frictional interference within the hexagonal hole 70 such that the screw hole plug is retained on the end of the hand tool as the tool is withdrawn from the vicinity of the acetabular shell.

Figure 9:
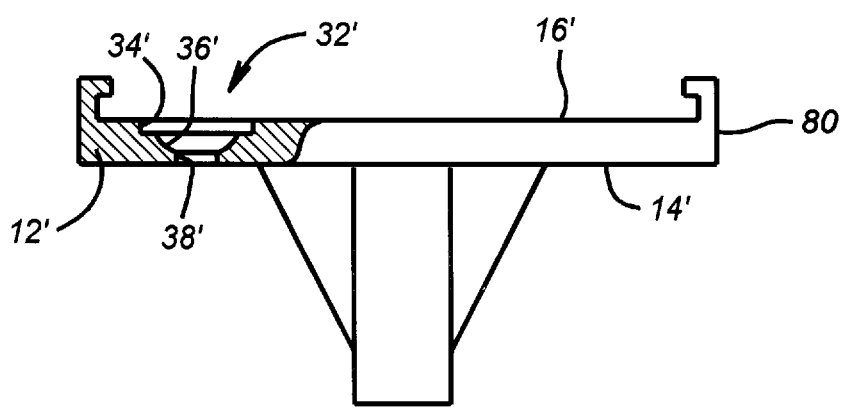
FIG. 9 is an elevation view, partially is section, showing a tibial component constructed in accordance with the present invention, comprising a second embodiment of the invention.

Referring to FIG. 9, there is illustrated, in partial cross-section, a second embodiment of the present invention, in the form of a tibial baseplate component 80 of an implantable total knee prosthesis. Plate 80 includes a screw hole 32' that is substantially similar to the screw hole 32 described above in the context of an acetabular shell, for receiving the above described screw hole plug 62. Other portions of the above-described screw hole 32 are indicated by like primed reference numerals. The second embodiment of FIG. 9 differs from the first described embodiment of FIGS. 1–8 principally in that the wall 12' through which screw hole 32' extends is planar, rather than hemispherical, and the proximal end 72 of the screw hole plug 62 can be planar, rather than spherical. In other pertinent respects, the above description of the first embodiment applies as well to the second embodiment of FIG. 9.

The present invention has been illustrated and described with particularity in terms of preferred embodiments. Nevertheless, it should be understood that no limitation of the scope of the invention is intended thereby. The scope of the invention is defined by the claims appended hereto. It should also be understood that variations of the particular embodiments described herein incorporating the principles of the present invention will occur to those of ordinary skill in the art and yet be within the scope of the appended claims.

I claim:

1. An implantable orthopedic prosthesis comprising, a prosthetic component having a wall, said wall having a first surface for engaging bone and a second surface; said wall defining a hole therethrough extending from said second surface to said first surface;

at least a portion of said hole being, in transverse cross-section, non-circular and having a major axis and a minor axis;

a plug;

at least a portion of said plug being, in transverse cross-section, non-circular and having a major axis and a minor axis;

said portion of said plug being sized to fit without interference within said portion of said hole if said respective major and minor axes of said plug and hole are substantially aligned; and said portion of said plug being sized to fit in locked interference within said portion of said hole if said respective major and minor axes of said plug and hole are substantially misaligned;

whereby said plug can be freely inserted into and removed from said hole with said respective major and minor axes of said plug and hole substantially aligned, and said plug can be interference-locked in said hole by rotating said plug relative to said hole to render said respective major and minor axes of said plug and hole substantially misaligned.

2. The implantable orthopedic prosthesis of claim 1, in which said non-circular portion of said hole is oval.

3. The implantable orthopedic prosthesis of claim 1, in which said non-circular portion of said plug is oval.

4. The implantable orthopedic prosthesis of claim 2, in which said non-circular portion of said plug is oval.

5. The implantable orthopedic prosthesis of claim 2, in which said oval portion is defined at least in part by two arc-sections of like radius.

6. The implantable orthopedic prosthesis of claim 3, in which said oval portion is defined at least in part by two arc-sections of like radius.

7. The implantable orthopedic prosthesis of claim 4, in which said oval portion is defined at least in part by two arc-sections of like radius.

8. The implantable orthopedic prosthesis of claim 5, in which said arc-sections each subtend 180° and are connected by straight sections lying parallel to said major axis.

9. The implantable orthopedic prosthesis of claim 6, in which said arc-sections each subtend 180° and are connected by straight sections lying parallel to said major axis.

10. The implantable orthopedic prosthesis of claim 7, in which said arc-sections each subtend 180° and are connected by straight sections lying parallel to said major axis.

11. The implantable orthopedic prosthesis of claim 2, in which said non-circular portion is cylindrical.

12. The implantable orthopedic prosthesis of claim 3, in which said non-circular portion is cylindrical.

13. The implantable orthopedic prosthesis of claim 4, in which said portions of said plug and hole have diametrical dimensions along their respective major axes that differ by a first amount, and said portions of said plug and hole have diametrical dimensions along their respective minor axes that differ by a second amount, said first and second amounts being substantially equal.

14. The implantable orthopedic prosthesis of claim 1, in which said hole includes a second portion that is circular in transverse cross-section.

15. The implantable orthopedic prosthesis of claim 14, in which said plug includes a second portion that is circular in transverse cross-section.

16. The implantable orthopedic prosthesis of claim 15, in which said circular portion of said plug is sized to fit in piloting engagement within said circular portion of said hole.

17. The implantable orthopedic prosthesis of claim 1, in which said plug includes a tool-engaging hole therein that is non-circular in cross-section.

18. The implantable orthopedic prosthesis of claim 4, in which said plug includes a tool-engaging hole therein that is non-circular in cross-section.

* * * * *